United States Patent
Wiederin et al.

(10) Patent No.: US 10,379,132 B1
(45) Date of Patent: Aug. 13, 2019

(54) AUTO-SAMPLING SYSTEM WITH INLINE PREPARATION OF CONCENTRATED SULFURIC ACID AND PHOSPHORIC ACID FOR ANALYTIC ELEMENTAL DETERMINATION

(71) Applicant: Elemental Scientific, Inc., Omaha, NE (US)

(72) Inventors: Daniel R. Wiederin, Omaha, NE (US); Nathan Saetveit, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 0 days.

(21) Appl. No.: 15/664,390

(22) Filed: Jul. 31, 2017

Related U.S. Application Data

(63) Continuation-in-part of application No. 15/012,971, filed on Feb. 2, 2016.

(60) Provisional application No. 62/370,042, filed on Aug. 2, 2016, provisional application No. 62/110,741, filed on Feb. 2, 2015.

(51) Int. Cl.
| | |
|---|---|
| *G01N 21/73* | (2006.01) |
| *G01N 35/10* | (2006.01) |
| *G01N 35/00* | (2006.01) |
| *G01N 1/14* | (2006.01) |
| *G01N 1/38* | (2006.01) |
| *H01J 49/10* | (2006.01) |

(52) U.S. Cl.
CPC ........... *G01N 35/1065* (2013.01); *G01N 1/14* (2013.01); *G01N 1/38* (2013.01); *G01N 35/00584* (2013.01); *G01N 21/73* (2013.01); *H01J 49/105* (2013.01)

(58) Field of Classification Search
USPC .... 73/1.02, 1.03, 53.01, 61.43–61.61, 64.56, 73/863, 863.01, 863.03, 863.21, 864.81; 422/62, 63, 68.1–82.13; 356/36, 356/311–334; 436/8–19, 100–105, 436/119–123, 164–172; 435/130
See application file for complete search history.

(56) References Cited

U.S. PATENT DOCUMENTS

| | | | | |
|---|---|---|---|---|
| 4,520,108 | A * | 5/1985 | Yoshida | G01N 35/085 422/503 |
| 8,748,191 | B2 * | 6/2014 | Kraus | G01N 35/1095 422/501 |
| 2009/0068749 | A1 * | 3/2009 | Saini | G01N 33/20 436/76 |
| 2009/0136978 | A1 * | 5/2009 | Kojima | C12Q 1/32 435/15 |
| 2017/0281639 | A1 * | 10/2017 | Kawasaki | A61K 47/02 |

* cited by examiner

*Primary Examiner* — Robert R Raevis

(74) *Attorney, Agent, or Firm* — Kevin E. West; Advent, LLP

(57) ABSTRACT

The present disclosure is directed to an auto-sampling system with syringe, valve configurations, and control logic that allow automatic, inline preparation of concentrated sulfuric acid and concentrated phosphoric acid for analytic analyzes. In implementations, the auto-sampling system includes independent syringe pumps connected to a valve system to dynamically introduce carrier, diluent, buffer, and eluent flows according to one or more modes of operation.

20 Claims, 12 Drawing Sheets

Results for 85% Phosphoric Acid

| | Direct Analysis with Dilution | | Preconcentration / Matrix Removal KED Mode | | | Preconcentration / Matrix Removal DRC Mode | | |
|---|---|---|---|---|---|---|---|---|
| Element | Determined Concentration (Phosphoric) (ppb) | MDL (Phosphoric) (ppb) | Determined Concentration (ppb m⁻¹) | MDL (Phosphoric) (ppb) | IDL (DI Water) (ppb) | Determined Concentration (ppb m⁻¹) | MDL (Phosphoric) (ppb) | IDL (DI Water) (ppb) |
| Ti 48 | 109 | 6 | 1.8 | 0.4 | 0.1 | 1.9 | 0.3 | 0.02 |
| V 51 | 0.2 | 0.02 | 0.10 | 0.03 | 0.006 | 0.088 | 0.004 | 0.002 |
| Mn 55 | 1 | 0.2 | 0.58 | 0.11 | 0.06 | 0.50 | 0.03 | 0.004 |
| Fe 56 | 28 | 3 | 22.8 | 2.0 | 0.09 | 21.1 | 1.1 | 0.06 |
| Ni 58 | 17 | 3 | 11.8 | 0.5 | 0.02 | 11.5 | 0.6 | 0.02 |
| Co 59 | 2 | 1 | 0.27 | 0.03 | 0.002 | 0.254 | 0.01 | 0.001 |
| Cu 65 | 2 | 1 | 0.187 | 0.013 | 0.06 | 0.127 | 0.010 | 0.005 |
| Zn 66 | 10 | 8 | 7.4 | 0.6 | 0.09 | 6.3 | 0.3 | 0.02 |
| Cd 114 | 0.3 | 0.1 | 0.26 | 0.04 | 0.004 | 0.26 | 0.02 | 0.001 |
| Pb 208 | 0.3 | 0.05 | 0.131 | 0.013 | 0.003 | 0.130 | 0.003 | 0.002 |

FIG. 7

AUTO-SAMPLING SYSTEM WITH INLINE PREPARATION OF CONCENTRATED SULFURIC ACID AND PHOSPHORIC ACID FOR ANALYTIC ELEMENTAL DETERMINATION

CROSS-REFERENCE TO RELATED APPLICATIONS

The present application claims the benefit of 35 U.S.C. § 119(e) of U.S. Provisional Application Ser. No. 62/370,042, filed Aug. 2, 2016, and titled "AUTO-SAMPLING SYSTEM WITH INLINE PREPARATION OF CONCENTRATED SULFURIC ACID AND PHOSPHORIC ACID FOR ANALYTIC ELEMENTAL DETERMINATION." The present application is also a continuation-in-part under 35 U.S.C. § 120 of U.S. patent application Ser. No. 15/012,971, filed Feb. 2, 2016, and titled "AUTO-SAMPLING SYSTEM WITH AUTOMATIC MATRIX MATCHING CAPABILITY," which claims the benefit of 35 U.S.C. § 119(e) of U.S. Provisional Application Ser. No. 62/110,741, filed Feb. 2, 2015, and titled "AUTO-SAMPLING SYSTEM WITH AUTOMATIC MATRIX MATCHING CAPABILITY." U.S. Provisional Application Ser. Nos. 62/370,042 and 62/110,741, and U.S. patent application Ser. No. 15/012,971 are herein incorporated by reference in their entireties.

BACKGROUND

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like) for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. Prior or during transportation of the aliquot to the nebulizer, the sample aliquot may be mixed with hydride generation reagents and fed into a hydride gas/liquid separator that channels hydride and/or sample gas into the nebulizer. The aerosol generated by the nebulizer is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

The present disclosure is directed to an auto-sampling system with syringe, valve, and control logic configurations that allow automatic, inline preparation of concentrated sulfuric acid and concentrated phosphoric acid for analytic analyses (e.g., via ICPMS). In some embodiments, the system includes a first syringe configured to drive a carrier solution, a second syringe configured to drive a buffer, a third syringe configured to drive an eluent, and a plurality of selection valves fluidically coupled with the first, second, and third syringes. The selection valves (e.g., automated selection/selector valves) can be controlled by a computing system to direct fluid flows from the first, second, and third syringes according to one or more modes of operation.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 7 is a table of analytic determinations of elemental presence in concentrated phosphoric acid with different sample preparation methods, in accordance with embodiments of this disclosure.

DETAILED DESCRIPTION

Overview

Figure 1A:
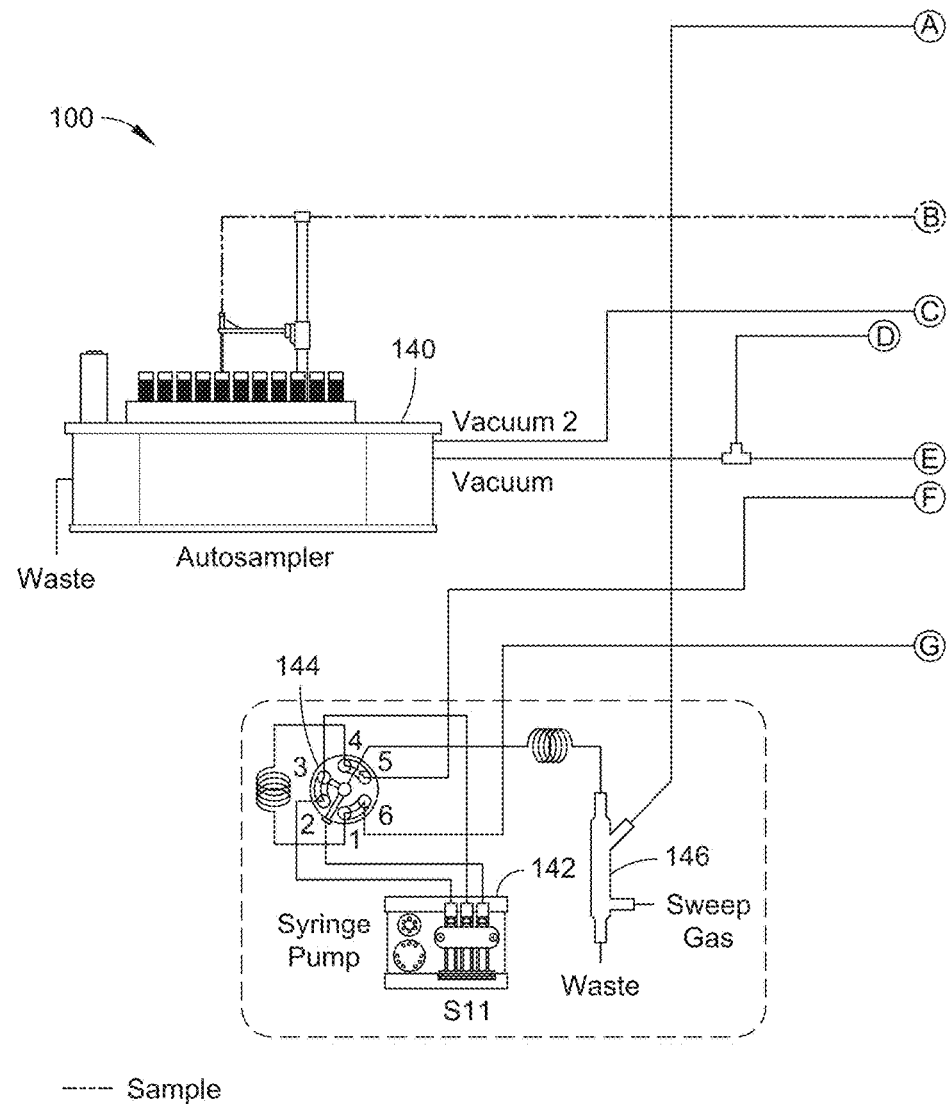
FIGS. 1A and 1B are schematics of an auto-sampling system operating in a sample loading mode, in accordance with an embodiment of this disclosure.
Figure 1B:
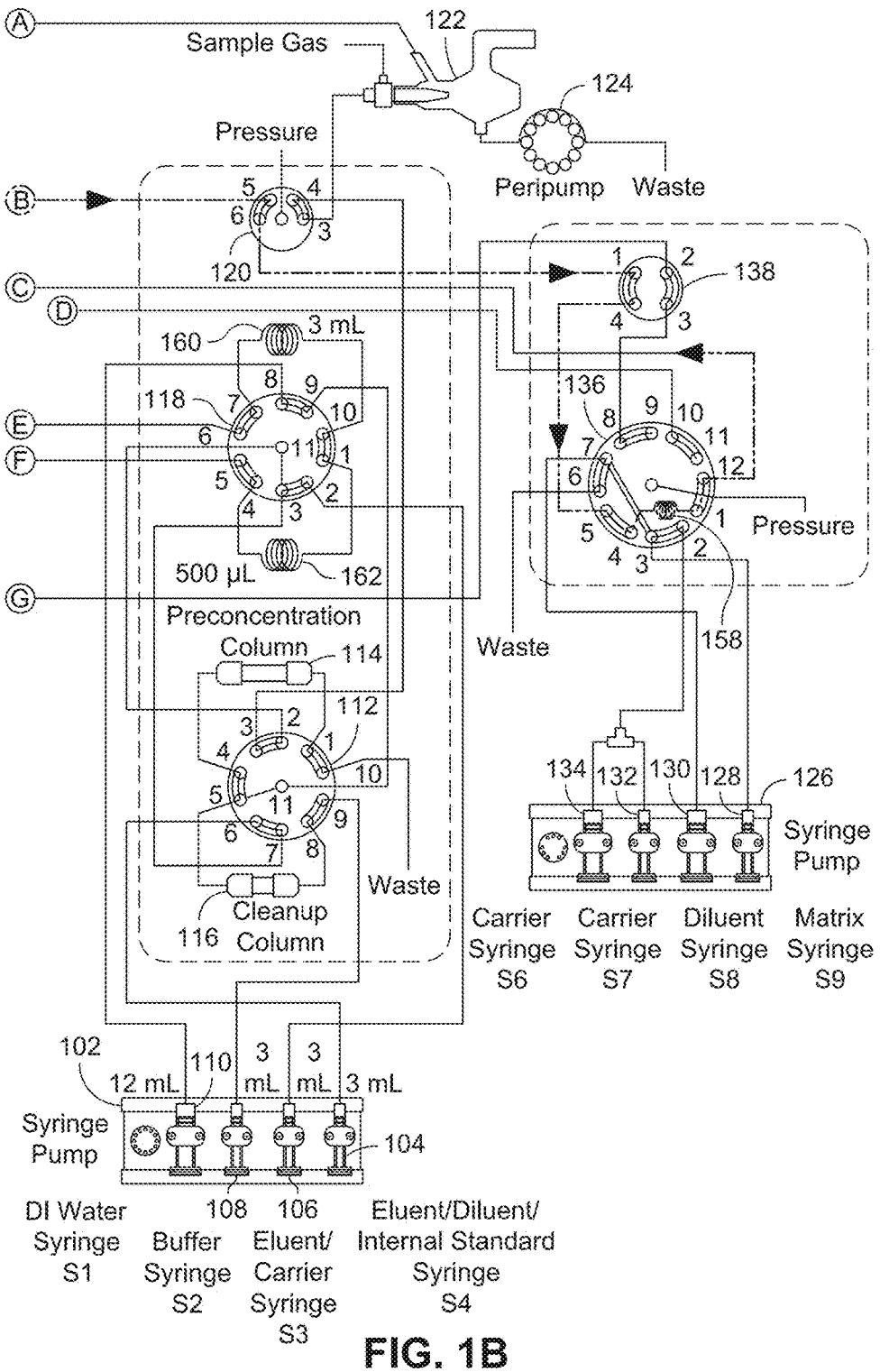
Figure 2A:
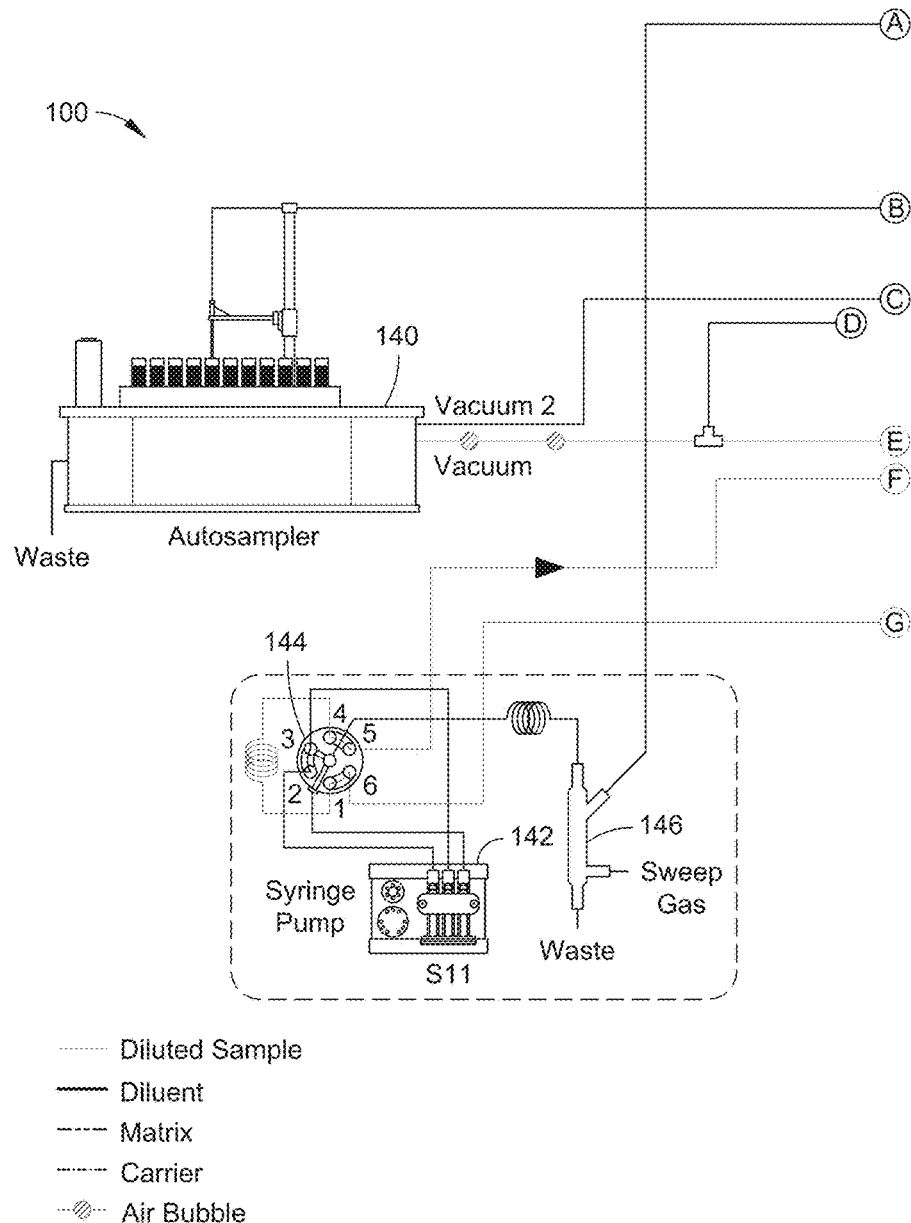
FIGS. 2A and 2B are schematics of an auto-sampling system operating in a sample dilution, matrix matching mode, in accordance with an embodiment of this disclosure.
Figure 2B:
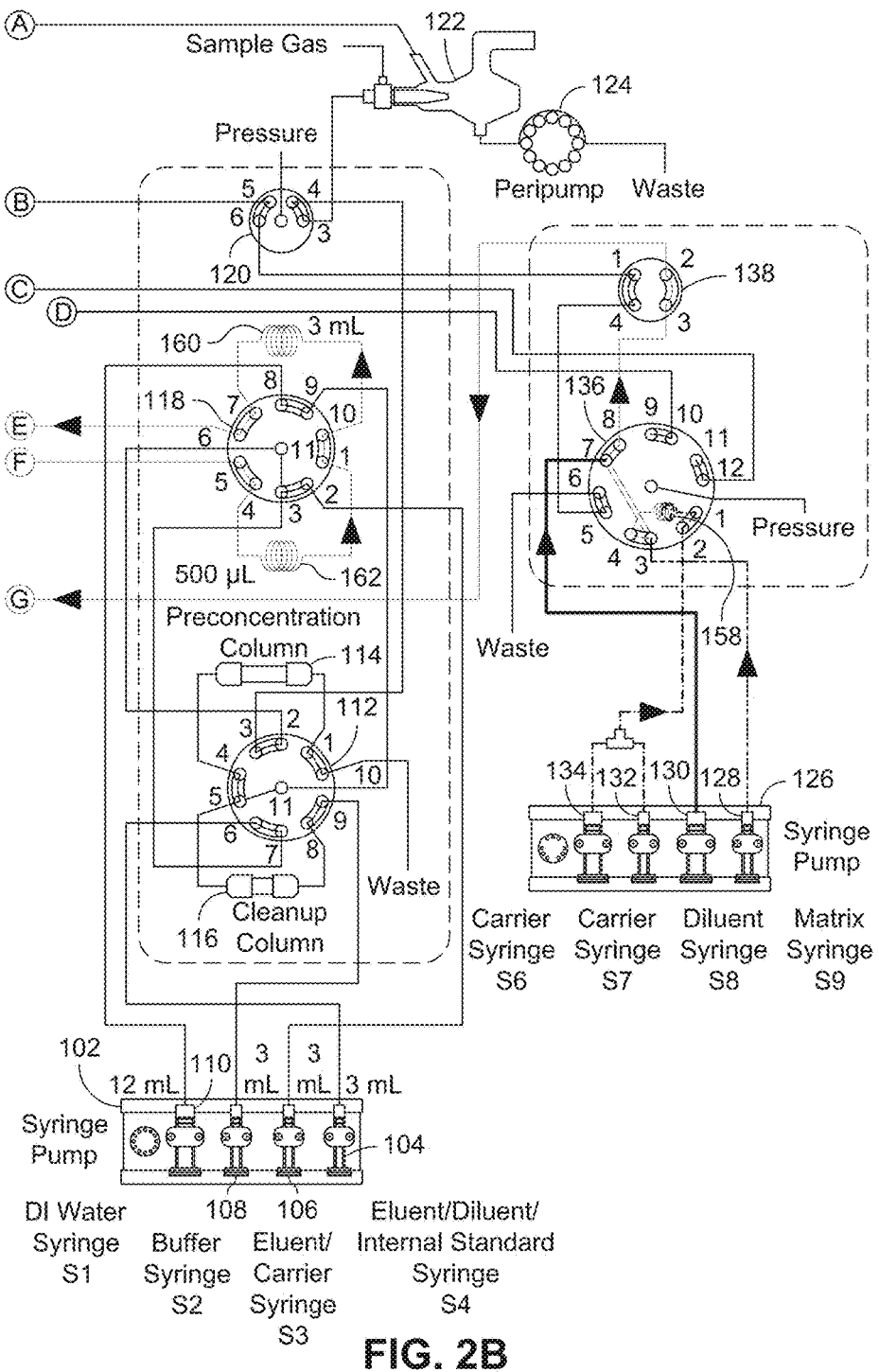
Figure 3A:
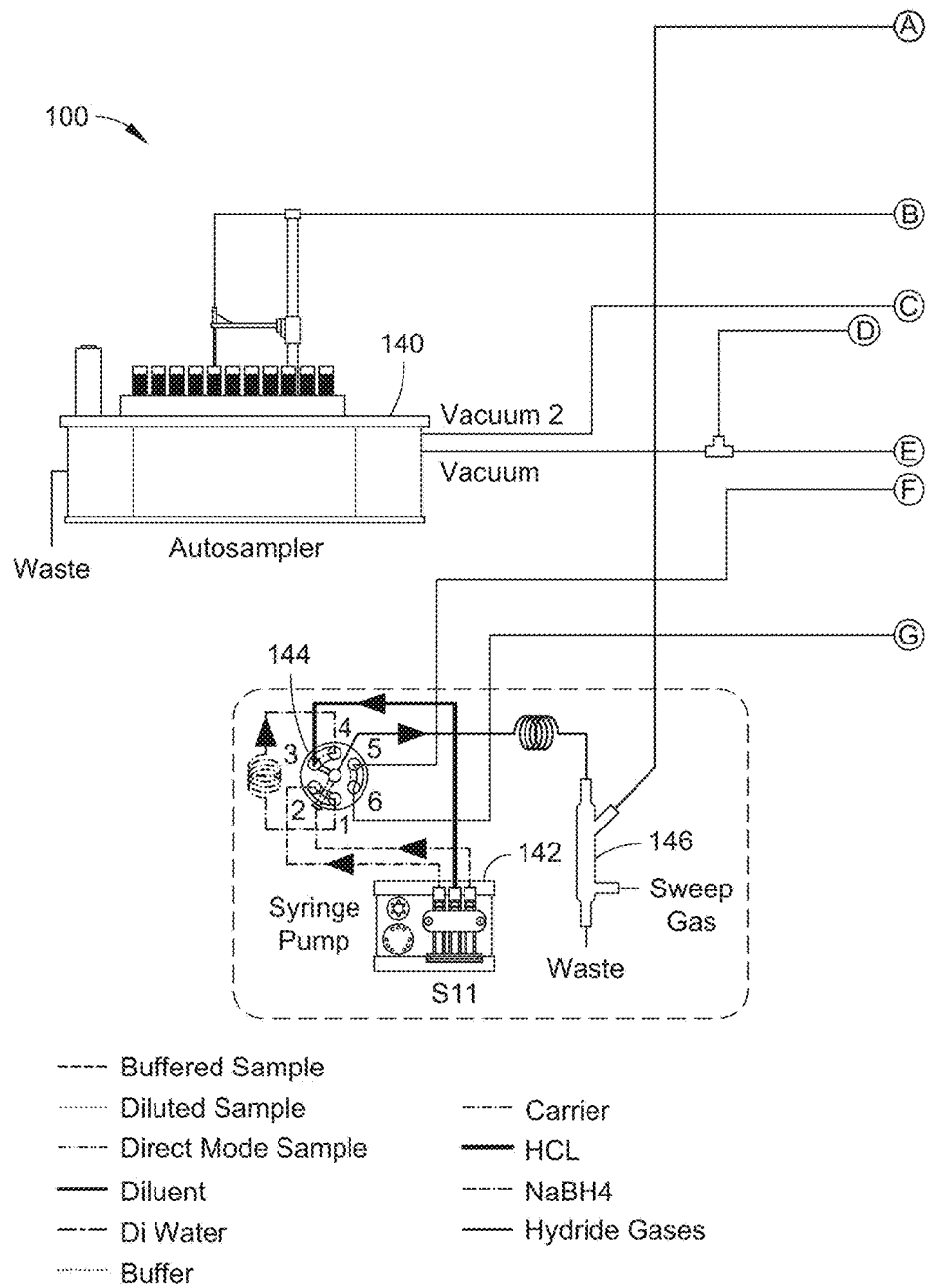
FIGS. 3A and 3B are schematics of an auto-sampling system operating in a hydride and/or direct dilution mode and/or pre-concentration column loading and matrix removal, in accordance with an embodiment of this disclosure.
Figure 3B:
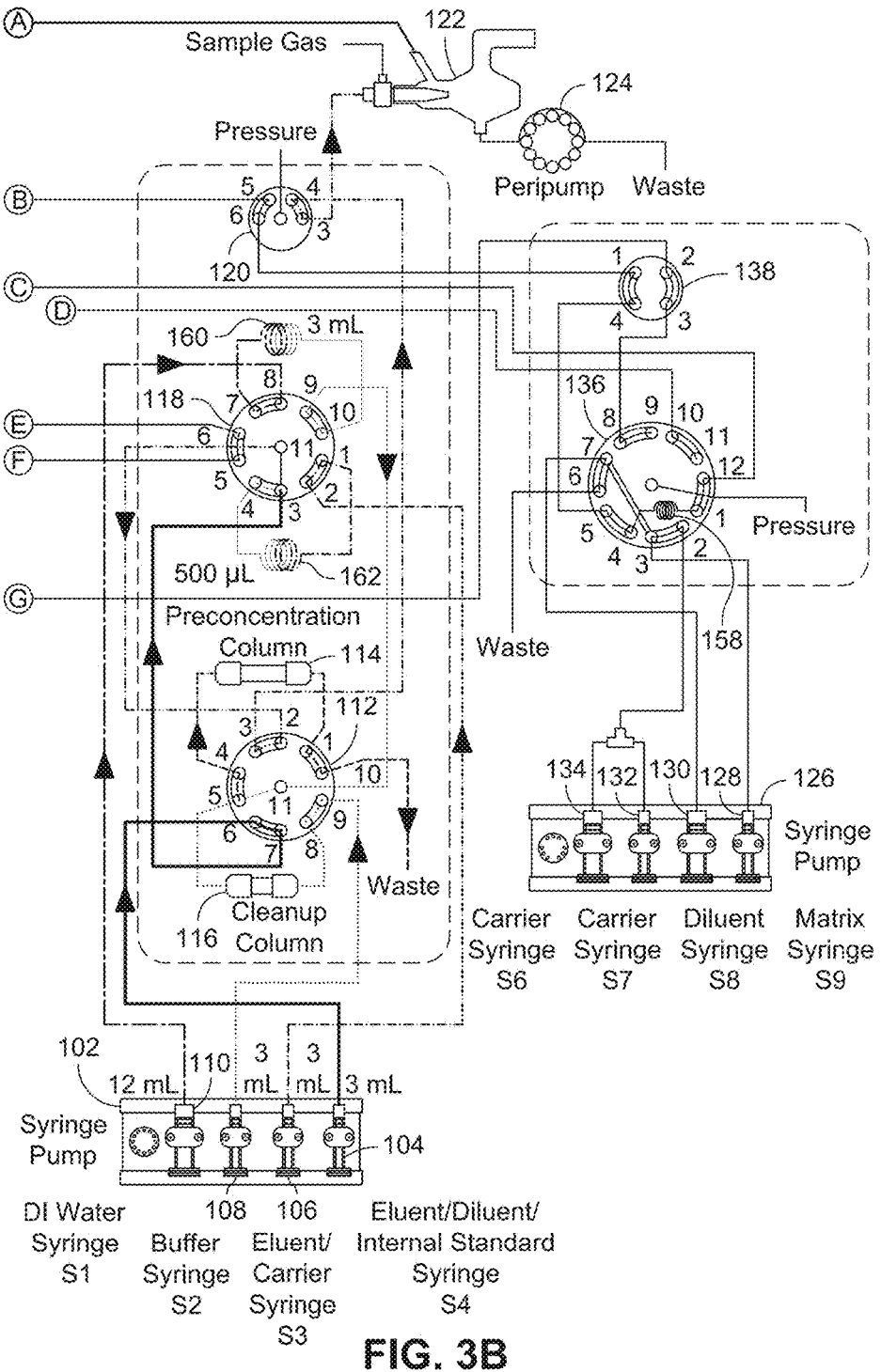
Figure 4A:
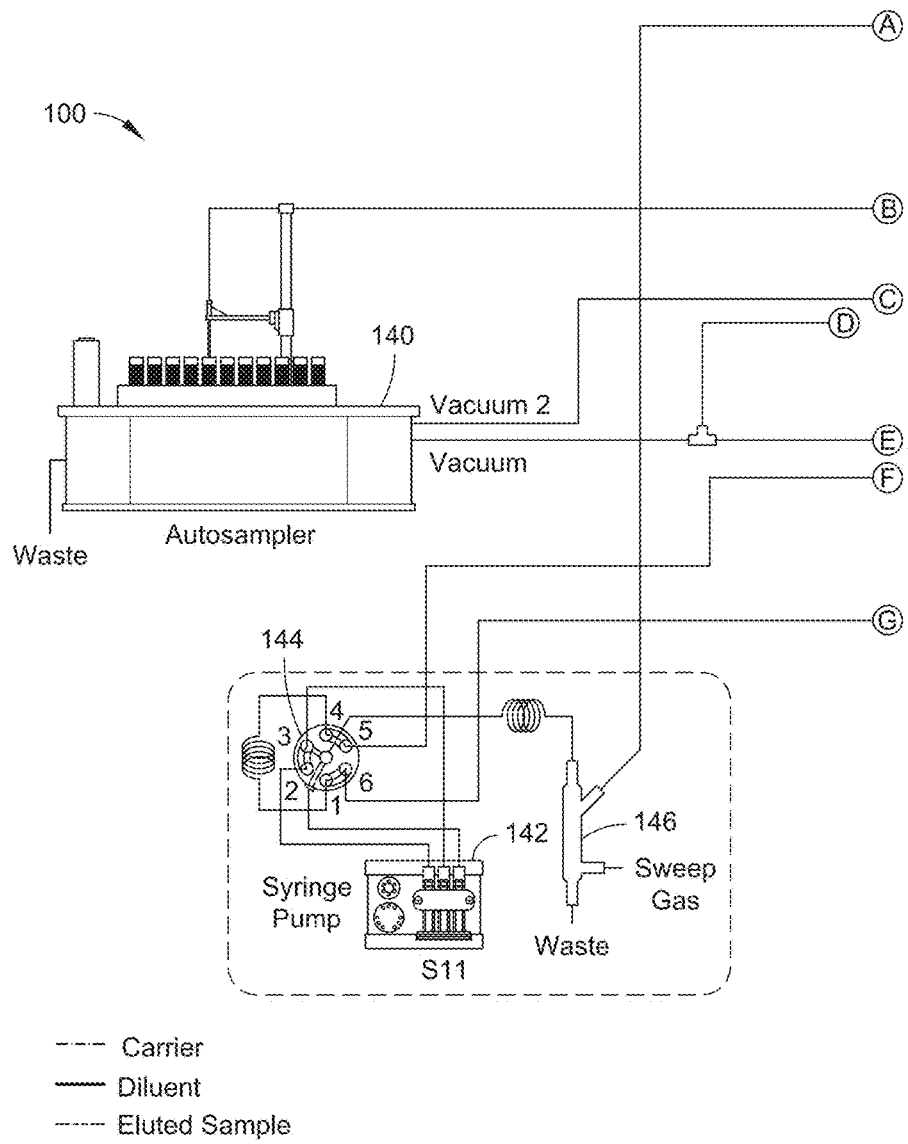
FIGS. 4A and 4B are schematics of an auto-sampling system operating in a pre-concentration mode for analyte elution and column cleaning, in accordance with an embodiment of this disclosure.
Figure 4B:
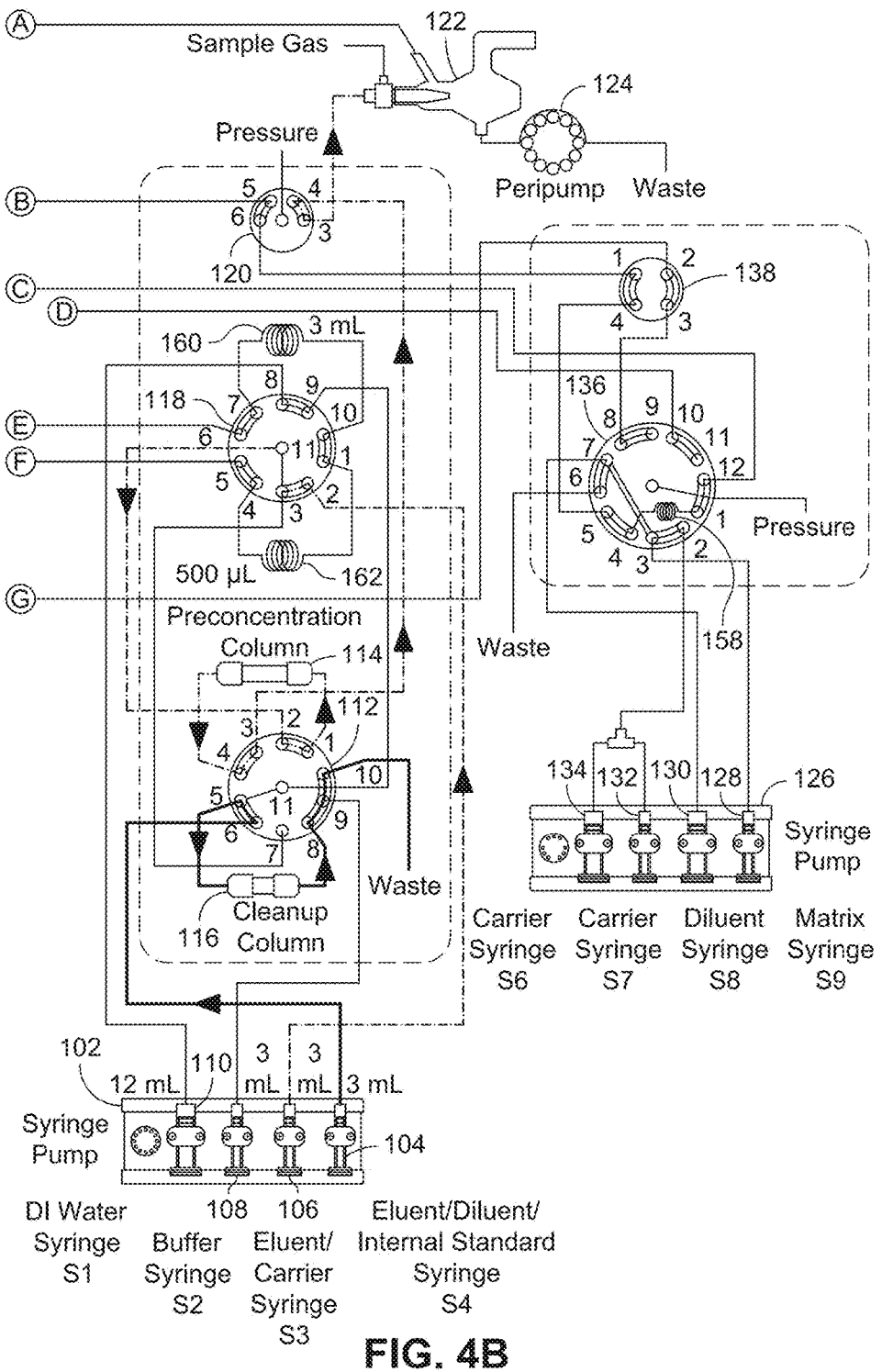

Determination of trace elemental concentrations or amounts in a sample can provide an indication of purity of the sample, or an acceptability of the sample for use as a reagent, reactive component, or the like. For instance, in certain manufacturing processes (e.g., semiconductor fabrication, pharmaceutical processing, etc.), the tolerances for impurities can be very strict, for example, on the order of fractions of parts per billion. For determination of trace elements in concentrated acids, such as concentrated sulfuric acid and concentrated phosphoric acid, the viscous and corrosive nature of the sample, and the presence of the corresponding sample matrices (e.g., acid matrices having anionic components of $SO_4^{2-}$, $PO_4^{3-}$, etc.), can inhibit manual handling of the sample and can introduce error in the analytic results of manually-manipulated samples. For instance, manual manipulation of a concentrated acid can include one or more evaporation techniques (e.g., evaporating the sample to dryness), dilution techniques (e.g., dilution in deionized water), chemical addition techniques (e.g., adding a chemical or mixture of chemicals (e.g., an acid, a peroxide, an internal standard spike, etc.), reconstituting techniques (e.g., reconstituting with nitric acid), or combinations thereof, where each step can introduce error via manual handling of the sample. Moreover, such manual techniques can require substantial time requirements, which can be prohibitive of substantial throughput, particularly where instruments such as graphite furnace atomic absorption spectrometers (GFAA) and Inductively Coupled Plasma Mass Spectrometers (ICP/ICP-MS) are ultimately used to analyze the samples.

An auto-sampling system is disclosed with syringe, valve, and control logic configurations that allow automatic, inline preparation of concentrated sulfuric acid and concentrated phosphoric acid for analytic analyses. This can be accomplished with independent syringe pumps connected to a valve system to dynamically introduce carrier, diluent, buffer, and eluent flows, as discussed in further detail below.

Example Implementations

FIGS. 1A through 5B illustrate an auto-sampling system 100 in accordance with various embodiments of this disclosure, wherein the auto-sampling system 100 includes syringe, valve, and control logic configurations that allow automatic, inline matrix matching of calibration standards to samples, and automatic, inline preparation of concentrated sulfuric acid and concentrated phosphoric acid for analytic analyses, via providing varying flow path configurations to transfer a variety of fluids through the auto-sampling system 100. Those skilled in the art will appreciate that the embodiments illustrated in the drawings and/or described herein may be modified or fully or partially combined to result in additional embodiments. Accordingly, the illustrated and described embodiments should be understood as explanatory and not as limitations of the present disclosure.

Figure 5A:
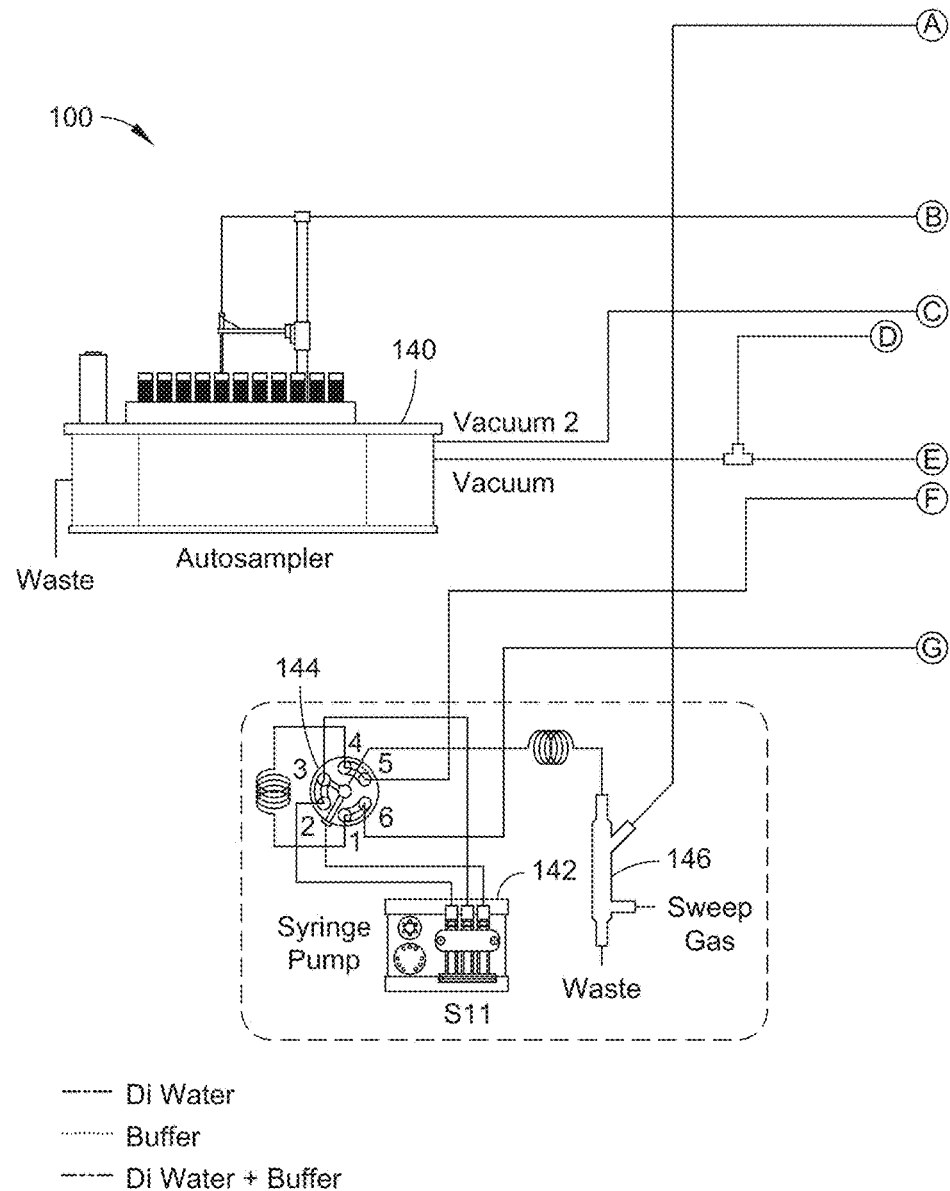
FIGS. 5A and 5B are schematics of an auto-sampling system operating in a column conditioning mode, in accordance with an embodiment of this disclosure.
Figure 5B:
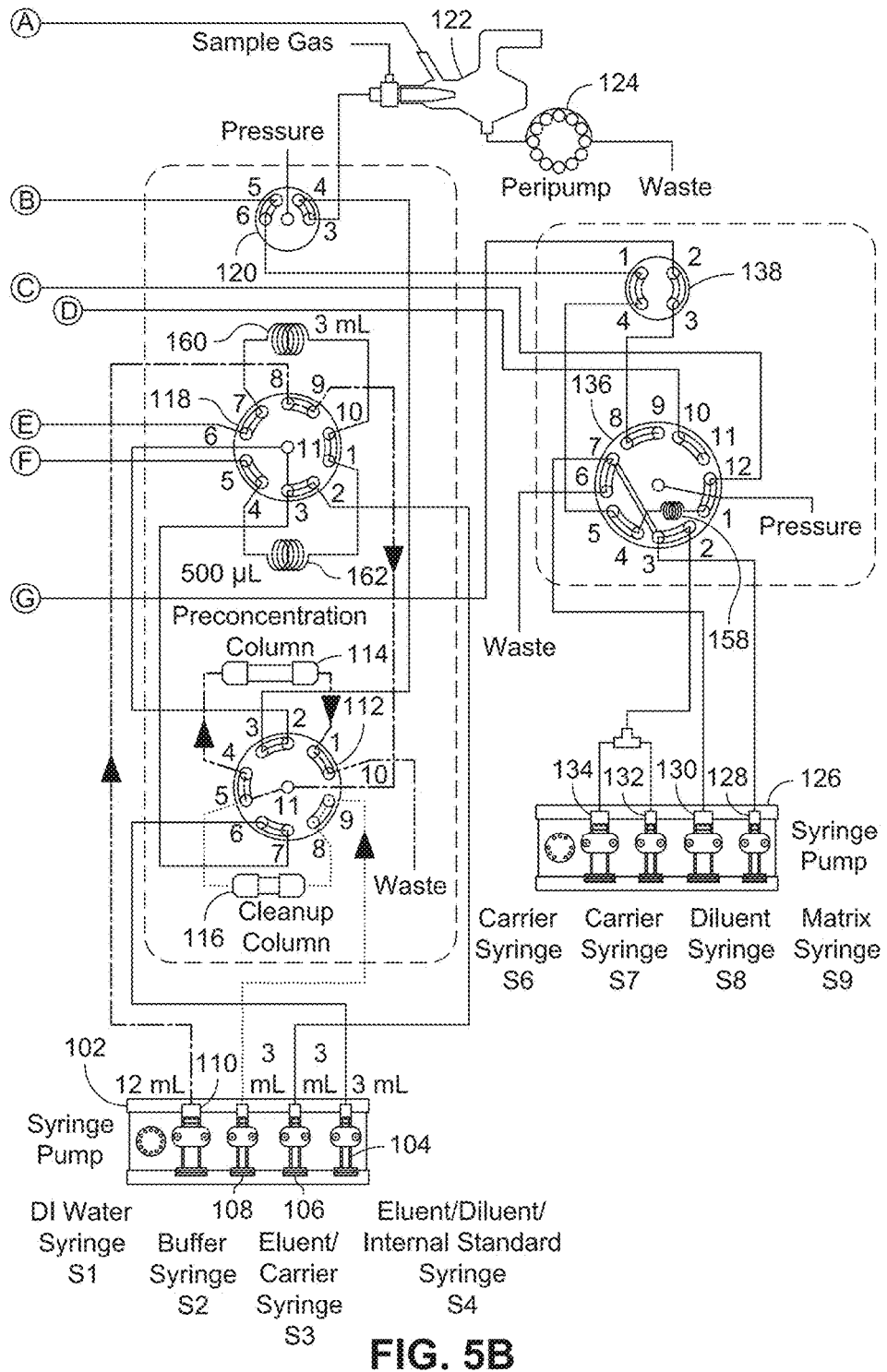

Example modes of operation are shown in FIGS. 1A through 5B. For example, FIGS. 1A and 1B illustrate the auto-sampling system 100 operating in a sample loading mode. FIGS. 2A and 2B illustrate the auto-sampling system 100 operating in a sample dilution, matrix matching mode. FIGS. 3A and 3B illustrate the auto-sampling system 100 operating in a hydride and/or direct dilution mode and/or pre-concentration column loading and matrix removal. FIGS. 4A and 4B illustrate the auto-sampling system 100 operating in a pre-concentration mode for analyte elution and column cleaning. FIGS. 5A and 5B illustrate the auto-sampling system 100 operating in a column conditioning mode.

In the embodiments illustrated in FIGS. 1A through 5B, the auto-sampling system 100 is shown to include a first syringe pump 102 that controls and/or physically supports a syringe 104 (e.g., a 3 mL syringe) configured to drive an eluent, diluent, or internal standard, a syringe 106 (e.g., a 3 mL syringe) configured to drive an eluent or a carrier, a syringe 108 (e.g., a 3 mL syringe) configured to drive a buffer, and a syringe 110 (e.g., a 12 mL syringe) configured to drive deionized (DI) water. In some embodiments, syringes 104, 106, 108, and 110 can be controlled by respective (independent) syringe pumps or at least one of syringes 104, 106, 108, and 110 can be controlled by a first pump, at least one of syringes 104, 106, 108, and 110 can be controlled by a second pump, and so forth. This applies to any other syringe pump configurations described herein.

Syringes 104 and 108 may be fluidically coupled to a selection valve 112 (e.g., an automated selection/selector valve), and syringes 106 and 110 may be fluidically coupled to another (second) selection valve 118. Selection valve 112 can also be coupled to a pre-concentration column 114, a trace metals cleanup column 116, a waste line and/or receptacle, selection valve 118, and another (third) selection valve 120. Selection valve 118 can also be coupled to a sampling device 140 and another selection valve 144. In embodiments, selection valve 144 is coupled to a hydride syringe pump 142 that can control syringes configured to drive hydride generation reagents (e.g., HCl and $NaBH_4$) and a carrier. Selection valve 144 can also be coupled with a gas/liquid separator 146 configured to isolate gaseous or aerosolized substances from the selection valve 144 and direct the gaseous or aerosolized substances to a spray chamber 122.

The spray chamber 122 is also configured to receive one or more sample substances from the sampling device 140 (e.g., automated sampling device), wherein the one or more sample substances can be received via selection valve 120, directly from the sampling device 140 or after the one or more sample substances have been directed through a mixing path defined by the network of selection valves. In some embodiments, a nebulizer is coupled to or included within the spray chamber 122 to aerosolize substances received from selection valve 120. The spray chamber 122 can also be coupled to a waste line and/or receptacle, where waste materials can be removed from the spray chamber by a pump 124 (e.g., peristaltic pump) coupled to the waste line. The spray chamber 122 can be included within or coupled to an analysis instrument, such as an ICP spectrometry instrument (e.g., ICP-MS, ICP-OES, ICP-AES, or the like). The spray chamber 122 may be configured to direct at least a portion of the one or more sample substances (e.g., gaseous or aerosolized sample substances) to an analysis site (e.g., torch or plasma site) of the analysis instrument.

In embodiments, the auto-sampling system 100 also includes syringe and valve configurations (and control logic, e.g., program instructions executable by a processor from a non-transitory computer readable carrier medium) that allow automatic, inline matrix matching of calibration standards to samples. For example, the system 100 includes another syringe pump 126 controlling a syringe 128 configured to drive a matrix solution, a syringe 130 configured to drive diluent, and one or more syringes 132 and/or 134 configured to drive carrier solution(s). Syringes 128, 130, 132, and 134 can be coupled to a selection valve 136. Selection valve 136 can also be coupled with a waste line and/or receptacle, a gas (e.g., Ar or $N_2$) source, another selection valve 138, and with the sampling device 140. Selection valve 138 may also be coupled with selection valve 120 (connecting to spray chamber 122) and with selection valve 144 (connecting to hydride syringe pump 142).

In some embodiments, the inline matrix matching is implemented by at least three independent syringes (i.e., syringes 128, 130, and 132 and/or 134) connected to a valve system (i.e., selection valve 136 and other fluidically coupled selection valves) to dynamically introduce carrier, diluent, and ultrapure stock matrix flows for each blank/standard/sample. Some example implementations include the following:

1) For "clean" stock calibration standard, blank, QC standards, or samples: Carrier+Matrix; Matrix flow rate set to achieve a pre-set final matrix concentration.

2) For samples that have matrix less than the pre-set matrix concentration, but more than "0" matrix: Carrier+Diluent+Matrix; Matrix addition is reduced as necessary.
3) For samples already containing at least the pre-set matrix concentration and analyzed undiluted: Carrier+Diluent. Diluent makes up the volume necessary to achieve the same total volume as condition #1.
4) For samples containing the pre-set matrix concentration but automatically diluted inline (which also dilutes the sample matrix): Same as condition #2.
5) For samples containing more than the pre-set matrix concentration, but automatically diluted inline (which also dilutes the sample matrix): Same as condition #2 OR condition #3.

This auto matrix matching functionality allows QC blanks and standards to be auto-calibrated and run from clean solutions (i.e., 1% nitric acid), while running real-world samples with high matrix. At the instrument (e.g., analysis instrument receiving one or more sample substances from spray chamber 122), all samples have a similar matrix composition, which allows more accurate quantification.

Figure 6:
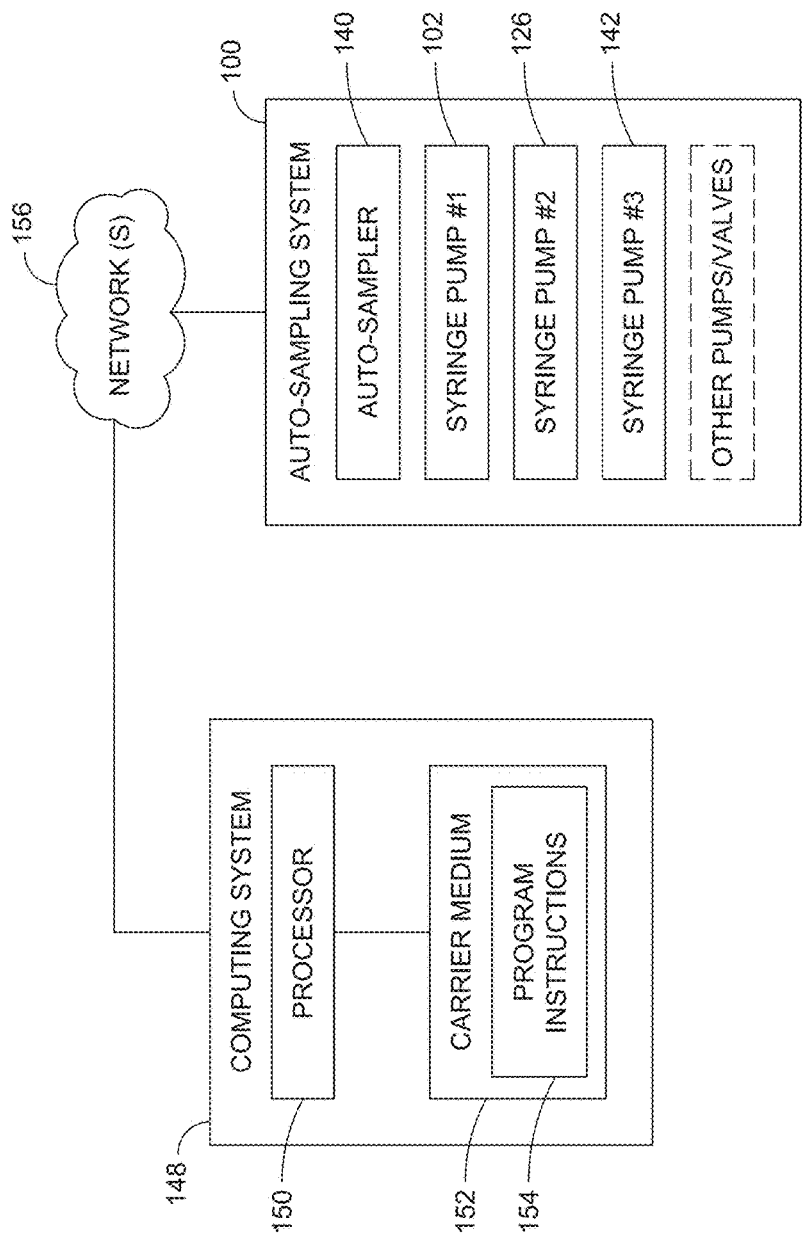
FIG. 6 is a block diagram illustrating a computing system for controlling an auto-sampling system, such as the auto-sampling system shown in FIGS. 1A through 5B.

Electromechanical devices (e.g., electrical motors, servos, actuators, or the like) may be coupled with or embedded within the selection valves to facilitate automated operation via control logic embedded within or externally driving the system 100. The electromechanical devices can be configured to cause the plurality of valves to direct fluid flows from syringes 128, 130, 132, and 134, and from other syringes, flow paths, etc., according to one or more modes of operation. As shown in FIG. 6, the auto-sampling system 100 may be controlled by a computing system 148 having a processor 150 configured to execute computer readable program instructions 154 (i.e., the control logic) from a non-transitory carrier medium 152 (e.g., storage medium such as a flash drive, hard disk drive, solid-state disk drive, SD card, optical disk, or the like). The computing system 148 can be connected to various components of the auto-sampling system 156, either by direct connection, or through one or more network connections (e.g., local area networking (LAN), wireless area networking (WAN or WLAN), one or more hub connections (e.g., USB hubs), and so forth). For example, the computing system 148 can be communicatively coupled to the sampling device 140, syringe pump 102, syringe pump 126, syringe pump 142, and any of the various pumps or selection valves described herein. The program instructions 154, when executing by processor 150, can cause the computing system 148 to control the auto-sampling system 100 (e.g., control the pumps and selection valves) according to one or more modes of operation, as described below.

In some embodiments, a first mode of operation is associated with one or more stock calibration standards, blanks, quality control standards, or samples. In the first mode of operation, selection valve 136 and other fluidically coupled valves regulate fluid flow of the carrier solution from syringe 132 and/or syringe 134 and the matrix solution from syringe 128. In the first mode of operation, the computing system 148 can be configured to select a fluid flow rate of the matrix solution that achieves a pre-set final matrix concentration.

In some embodiments, a second mode is associated with one or more samples containing matrix solution below a pre-set matrix concentration. In the second mode of operation, selection valve 136 and other fluidically coupled valves regulate fluid flow of the carrier solution from syringe 132 and/or syringe 134, the diluent from syringe 130, and the matrix solution from syringe 128. In the second mode of operation, the computing system 148 can be configured to reduce fluid flow of the matrix solution until a (predefined or programmed) threshold matrix concentration is achieved.

In some embodiments, a third mode of operation is associated with one or more undiluted samples containing a pre-set concentration of matrix solution. In the third mode of operation, selection valve 136 and other fluidically coupled valves regulate fluid flow of the carrier solution from syringe 132 and/or syringe 134 and the diluent from syringe 130. In the third mode of operation, the computing system 148 can be configured to cause a selected volume of diluent to be introduced to achieve a pre-set final matrix concentration.

In some embodiments, a fourth mode of operation is associated with one or more samples containing a pre-set concentration of matrix solution, where the one or more samples are diluted inline (causing the sample matrix to also be diluted). In the fourth mode of operation, selection valve 136 and other fluidically coupled valves regulate fluid flow of the carrier solution from syringe 132 and/or syringe 134, the diluent from syringe 130, and the matrix solution from syringe 128. In the fourth mode of operation, the computing system 148 can be configured to reduce the fluid flow of the matrix solution when a (predefined or programmed) threshold matrix concentration is achieved.

In some embodiments, a fifth mode of operation is associated with one or more samples containing matrix solution above a pre-set matrix concentration, where the one or more samples are diluted inline (causing the sample matrix to also be diluted). In the fifth mode of operation, selection valve 136 and other fluidically coupled valves regulate fluid flow of the carrier solution from syringe 132 and/or syringe 134, the diluent from syringe 130, and the matrix solution from syringe 128. In the fifth mode of operation, the computing system 148 can be configured to reduce or stop fluid flow of the matrix solution when a (predefined or programmed) threshold matrix concentration is achieved.

In some embodiments, the system 100 is configured to run samples using either: external automatic inline matrix matching (as described above) with three independent syringes for carrier, diluent, and matrix solutions; or automated method of standard additions with three independent syringes for sample, diluent, and spike solutions. Method of Standard Addition (MSA) is an analytical technique that uses a sample as its own "matrix match." Variable spikes of standard are added to the same volume of sample to create a calibration curve in the true sample matrix. The absolute value of the X-intercept is then calculated to be the concentration of an element in the original sample. MSA is considered as the most accurate type of matrix matching, but it requires that a sample be measured multiple times (unspiked and spiked at various concentrations), which significantly reduces sample throughput and increases cost of analysis. However, MSA provides can be the best option for samples that require the highest level of accuracy and/or do not have a suitable ultrapure external matrix matching solution.

In some embodiments, the system 100 is further configured to run in a sixth mode of operation for MSA matching, where syringe 128 is configured to drive a spike solution in place of the matrix solution. In the sixth mode of operation, selection valve 136 and other fluidically coupled valves regulate fluid flow of the carrier solution from syringe 132 and/or syringe 134, the diluent from syringe 130, and the spike solution from syringe 128. In the sixth mode of operation, the computing system 148 can be configured to control fluid flow from each syringe according to a MSA algorithm.

In some embodiments, the system 100 is configured for inline preparation of concentrated sulfuric acid and concentrated phosphoric acid for analytic analyses (e.g., via ICPMS). Such preparation generally involves preconcentration and matrix removal to process the concentrated sulfuric acid or concentrated phosphoric acid for introduction to a spray chamber 122 that can be included within or coupled to an analysis instrument, such as an ICP spectrometry instrument (e.g., ICP-MS, ICP-OES, ICP-AES, or the like). The inline preparation of concentrated sulfuric acid and concentrated phosphoric acid can include loading of an undiluted, concentrated phosphoric acid (e.g., 85% $H_3PO_4$) or of an undiluted, concentrated sulfuric acid (e.g., 98% $H_2SO_4$) into fluid lines within the auto-sampling system 100, such as onto a loop associated with the selection valve 136 (e.g., loop 158). For example, the loading can involve the first mode of operation of the auto-sampling system 100, described with reference to FIGS. 1A and 1B. In implementations, the concentrated acid sample can be diluted prior to introduction of the sample to the auto-sampling system 100 (e.g., via the sampling device 140), such as through a manual dilution of concentrated sulfuric acid or concentrated phosphoric acid prior to introduction to the system 100 (e.g., via the sampling device 140), or otherwise diluting the concentrated sulfuric acid or concentrated phosphoric acid prior to introduction to the system 100. In implementations, the concentrated acid sample can be partially diluted prior to introduction of the sample to the auto-sampling system 100, and then additionally diluted inline according to one or more autodilution modes described herein.

The inline preparation of concentrated sulfuric acid and concentrated phosphoric acid can also include autodilution of the sample into another loop of the autosampling system 100 (such as one or more of the loops associated with the selection valve 118, loop 160 and loop 162) to reduce the acid concentration of the sample (e.g., in implementations where the sample is not diluted prior to introduction of the sample to the auto-sampling system 100, such as an offline manual dilution). For example, the autodilution can involve the second mode of operation of the auto-sampling system 100, described with reference to FIGS. 2A and 2B. While the selection valve 118 is shown being associated with loop 160 as a 3 mL loop and with loop 162 as a 500 μL loop, the volume of the loops can vary depending on a desired diluted sample volume. For example, the volume of loop 160 can be greater than 3 mL (e.g., 4 mL, 5 mL, 6 mL, 7 mL, 8 mL, 9 mL, 10 mL, and so on) or less than 3 mL (e.g., 2.5 mL, 2.0 mL, 1.5 mL, 1.0 mL, 0.5 mL, and so on). Further, while the syringe 128 can be associated with a matrix syringe (e.g., in fluid communication with a matrix solution to introduce the matrix solution to the auto-sampling system 100), it is noted that the syringe 128 can additionally or alternatively be associated with a spike syringe (e.g., in fluid communication with a spike solution, such as a standard spike, to introduce the spike solution to the auto-sampling system 100). In implementations, loop 162 holds a sample for direct dilution analysis (e.g., according to the direct dilution mode associated with FIGS. 3A and 3B), where the sample can be diluted or further diluted at a mixing port (e.g., port 3 of the selection valve 118) prior to introduction to the spray chamber 122). In implementations, loop 160 holds a sample for subsequent buffering and preconcentration after displacement with a carrier fluid or DI water (e.g., via syringe 110). For example, the inline preparation of concentrated sulfuric acid and concentrated phosphoric acid can include automatic buffering of the diluted sample following displacement of the diluted sample from loop 160 and automatic loading of the buffered sample onto a preconcentration column (e.g., the preconcentration column 114) for the preconcentration of various elements (e.g., impurities including, but not limited to, titanium, vanadium, manganese, iron, nickel, cobalt, copper, zinc, cadmium, lead, etc., and combinations thereof) present in the concentrated acid and for removal of the acid matrix (e.g., acid matrices having anionic components of $SO_4^{2-}$, $PO_4^{3-}$, etc.). For example, the automatic buffering and loading can involve the third mode of operation of the auto-sampling system 100, described with reference to FIGS. 3A and 3B, whereby the diluted sample can mix with a buffer solution at a mixing port (e.g., port 5 of selection valve 112) to buffer the diluted sample prior to introduction to the preconcentration column 114. In implementations, the buffer solution is transferred through the cleanup column 116 prior to introduction to the diluted sample at the mixing port of the selection valve 112, to remove any trace metals from the buffer solution (e.g., such that trace metals from the buffer solution are not subsequently retained by the preconcentration column 114, introducing error to the trace elemental analysis of the diluted sample). In an implementation, the elements of interest for preconcentration in the preconcentration column 114 are chelated at neutral pH.

The inline preparation of concentrated sulfuric acid and concentrated phosphoric acid can also include eluting the preconcentrated elements into an analytic instrument, such as an ICP spectrometry instrument (e.g., ICP-MS, ICP-OES, ICP-AES, or the like), or into a container for later testing (e.g., a microtiter plate, a sample cup, a sample vial, or so forth). For example, the eluting can involve the fourth mode of operation of the auto-sampling system 100, described with reference to FIGS. 4A and 4B. The eluent can be introduced to the auto-sampling system 100 via the syringe 106, which in embodiments introduces an ultrapure acid solution (e.g., nitric acid, such as 10% $HNO_3$) to the preconcentration column 114 to remove the preconcentrated elements for analysis (e.g., via the spray chamber 122). Such analysis can involve dramatically attenuated matrix interferences due to the acid matrix removal accomplished via the third mode of operation. Example implementations of such attenuated matrix interferences are shown with respect to FIG. 7. In implementations, the eluent can be introduced to the auto-sampling system 100 via the syringe 106, which in embodiments introduces an ultrapure acid solution (e.g., nitric acid, such as 10% $HNO_3$) to the preconcentration column 114 to remove the preconcentrated elements for transfer into a container for later testing (e.g., a microtiter plate, a sample cup, a sample vial, or so forth).

Referring to FIG. 7, a table of analytic determinations of elemental presence in concentrated phosphoric acid (85% $H_3PO_4$) with different sample preparation methods is shown in accordance with embodiments of this disclosure. Without preconcentration and matrix removal (e.g., Direct Analysis with Dilution), the determined concentration and method detection limits (MDLs) of the elements is generally artificially high, which can be due to unresolved interferences from matrix elements. With preconcentration and matrix removal, the MDLs are greatly enhanced, such as shown in the Preconcentration/Matrix Removal KED (Kinetic Energy Discrimination) Mode and in the Preconcentration/Matrix Removal DRC (Dynamic Reaction Cell) Mode. For instance, the Preconcentration/Matrix Removal KED Mode utilizes the inline preparation of concentrated sulfuric acid and concentrated phosphoric acid via operation of the auto-sampling system 100 described herein, in combination with an ICPMS operating with an interference removal technique (KED), whereas the Preconcentration/Matrix Removal DRC Mode utilizes the inline preparation of concentrated sulfuric acid and concentrated phosphoric acid via operation of the auto-sampling system 100 described herein, in combination with an ICPMS operating with an interference removal technique (DRC). For each of the Preconcentration/Matrix Removal KED Mode and the Preconcentration/Matrix Removal DRC Mode, Instrument Detection Limit (IDL) was measured with deionized (DI) water blanks. Since DI water is clean, it provides an uninterrupted measure of the true detection limit of the inline preparation of concentrated sulfuric acid and concentrated phosphoric acid via operation of the auto-sampling system 100 described herein. For instance, since preconcentration and matrix removal with standard addition is matrix independent, the IDL in DI water is a realistic representation of what the system can determine in concentrated acid. For traditional/direct analysis, that may not be the case, due to the presence of the matrix which degrades the detection limit significantly. Comparison of the MDL for Direct Analysis with Dilution to the IDL for the Preconcentration/Matrix Removal techniques provides insight into the efficient handling of concentrated acid samples for determination of trace elements therein. It is noted that matrix removal facilitates usage of DRC mode on the ICPMS, since matrix-based interferences are attenuated. DRC mode can have higher sensitivity for analysis than KED mode, so the DRC detection limits tend to be superior to the KED mode detection limits.

It should be recognized that the various functions, control operations, processing blocks, or steps described throughout the present disclosure may be carried out by any combination of hardware, software, or firmware. In some embodiments, various steps or functions are carried out by one or more of the following: electronic circuitry, logic gates, multiplexers, a programmable logic device, an application-specific integrated circuit (ASIC), a controller/microcontroller, or a computing system. A computing system may include, but is not limited to, a personal computing system, a mobile computing device, mainframe computing system, workstation, image computer, parallel processor, or any other device known in the art. In general, the term "computing system" is broadly defined to encompass any device having one or more processors, which execute instructions from a carrier medium.

Program instructions implementing functions, control operations, processing blocks, or steps, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

Furthermore, it is to be understood that the invention is defined by the appended claims. Although embodiments of this invention have been illustrated, it is apparent that various modifications may be made by those skilled in the art without departing from the scope and spirit of the disclosure.

What is claimed is:

1. An automatic sampling system for preparation of sulfuric acid and phosphoric acid for analytic analyses, comprising:
    a sampling assembly configured to draw at least one of phosphoric acid or sulfuric acid;
    a first syringe configured to drive a carrier solution;
    a second syringe configured to drive a buffer;
    a third syringe configured to drive an eluent;
    a preconcentration column; and
    a plurality of selection valves fluidically coupled with the sampling assembly, the first syringe, the second syringe, the third syringe, and the preconcentration column, the plurality of selection valves being configured to direct fluid flows from the first syringe, the second syringe, and the third syringe according to a plurality of modes of operation to buffer a diluted sample of at least one of phosphoric acid or sulfuric acid to provide a buffered sample, direct the buffered sample to the preconcentration column to remove an acid matrix from the buffered sample and to provide a preconcentrated sample, and elute the preconcentrated sample for analysis.

2. The automatic sampling system of claim 1, wherein the sampling assembling is configured to draw at least one of undiluted, concentrated phosphoric acid or undiluted, concentrated sulfuric acid.

3. The automatic sampling system of claim 2, further comprising:
    a fourth syringe configured to drive a diluent, the fourth syringe coupled with the plurality of selection valves to introduce the diluent with the undiluted, concentrated phosphoric acid or undiluted, concentrated sulfuric acid to provide the diluted sample of at least one of phosphoric acid or sulfuric acid prior to buffering the diluted sample.

4. The automatic sampling system of claim 1, wherein the sampling assembling is configured to draw at least one of diluted phosphoric acid or diluted sulfuric acid.

5. The automatic sampling system of claim 1, wherein one or more elements of interest are chelated in the preconcentration column at a neutral pH.

6. The automatic sampling system of claim 5, wherein the one or more elements of interest at least one of titanium, vanadium, manganese, iron, nickel, cobalt, copper, zinc, cadmium, or lead.

7. The automatic sampling system of claim 1, further including at least a first loop coupled with two ports of a first selection valve of the plurality of selection valves and a second loop coupled with two ports of a second selection valve of the plurality of selection valves.

8. A method for preparation of sulfuric acid and phosphoric acid for analytic analyses, comprising:
    introducing a sample of at least one of phosphoric acid or sulfuric acid to a sample preparation system, the sample preparation system including a plurality of syringes to transfer fluid through the sample preparation system, a plurality of loops, and a plurality of selection valves providing a plurality of flow path configuration according to a plurality of modes of operation;
    introducing a buffer to the sample of at least one of phosphoric acid or sulfuric acid to buffer the sample at a mixing port of a selection valve of the plurality of selection valves;
    directing the buffered sample to a preconcentration column;
    removing an acid matrix from the buffered sample with the preconcentration column;
    chelating one or more elements of interest with the preconcentration column; and introducing an eluent to the preconcentration column to remove one or more chelated elements of interest and provide a preconcentrated sample for analysis.

9. The method of claim 8, further comprising:
introducing the preconcentrated sample to a spray chamber.

10. The method of claim 9, further comprising:
analyzing the preconcentrated sample with an inductively coupled plasma spectrometer.

11. The method of claim 10, wherein analyzing the preconcentrated sample with an inductively coupled plasma spectrometer includes analyzing the preconcentrated sample with an inductively coupled plasma spectrometer operating in a Kinetic Energy Discrimination (KED) mode.

12. The method of claim 10, wherein analyzing the preconcentrated sample with an inductively coupled plasma spectrometer includes analyzing the preconcentrated sample with an inductively coupled plasma spectrometer operating in a Dynamic Reaction Cell (DRC) mode.

13. The method of claim 8, wherein chelating one or more elements of interest with the preconcentration column includes chelating one or more elements of interest with the preconcentration column at a neutral pH.

14. An automatic sampling system for preparation of sulfuric acid and phosphoric acid for analytic analyses, comprising:
a first syringe configured to drive a carrier solution;
a second syringe configured to drive a buffer;
a third syringe configured to drive an eluent; and
a plurality of selection valves fluidically coupled with a sampling assembly, the first syringe, the second syringe, and the third syringe, the plurality of selection valves including a first selection valve fluidically coupled with a first loop, the first loop configured to receive a sample of at least one of at least one of phosphoric acid or sulfuric acid via the first selection valve, the plurality of selection valves including a second selection valve fluidically coupled with the first selection valve and a second loop, the second loop configured to receive the sample from the first loop via the second selection valve, the plurality of selection valves including a third selection valve fluidically coupled with the second selection valve and a preconcentration column, the third selection valve including a mixing port configured to receive a diluted sample from the second selection valve and a buffer driven by the second syringe to provide a buffered sample, the third selection valve configured to direct the buffered sample to the preconcentration column to remove an acid matrix from the buffered sample and to provide a preconcentrated sample in a first mode of operation and to direct an eluent into the preconcentration column in a second mode of operation to provide the preconcentrated sample for analysis.

15. The automatic sampling system of claim 14, wherein the sampling assembling is configured to draw at least one of undiluted, concentrated phosphoric acid or undiluted, concentrated sulfuric acid.

16. The automatic sampling system of claim 15, further comprising:
a fourth syringe configured to drive a diluent, the fourth syringe coupled with the second selection valve to introduce the diluent with the undiluted, concentrated phosphoric acid or undiluted, concentrated sulfuric acid to provide the diluted sample of at least one of phosphoric acid or sulfuric acid prior to buffering the diluted sample.

17. The automatic sampling system of claim 16, wherein the second selection valve includes a mixing port configured to receive the undiluted, concentrated phosphoric acid or undiluted, concentrated sulfuric acid and the diluent to provide the diluted sample.

18. The automatic sampling system of claim 14, wherein the sampling assembling is configured to draw at least one of diluted phosphoric acid or diluted sulfuric acid.

19. The automatic sampling system of claim 14, wherein one or more elements of interest are chelated in the preconcentration column at a neutral pH in the first mode of operation.

20. The automatic sampling system of claim 19, wherein the one or more elements of interest at least one of titanium, vanadium, manganese, iron, nickel, cobalt, copper, zinc, cadmium, or lead.

* * * * *